United States Patent
Smith et al.

(10) Patent No.: US 6,424,868 B1
(45) Date of Patent: *Jul. 23, 2002

(54) PORTABLE FUNCTIONAL ELECTRICAL STIMULATION (FES) SYSTEM FOR UPPER OR LOWER EXTREMITY APPLICATIONS

(75) Inventors: Brian T. Smith, Hatboro; Brian McGee, Elkins Park; John Douglas, Philadelphia; Randal R. Betz, Langhorne, all of PA (US); Michael Ignatoski, Ann Arbor, MI (US)

(73) Assignee: Shriners Hospital for Children, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/436,013

(22) Filed: Nov. 9, 1999

Related U.S. Application Data

(63) Continuation of application No. 09/184,780, filed on Nov. 2, 1998, now Pat. No. 5,983,140, which is a continuation of application No. 08/870,192, filed on Jun. 6, 1997, now Pat. No. 5,861,017.

(51) Int. Cl.[7] ................................................. A61N 1/08
(52) U.S. Cl. ........................................... 607/59; 607/49
(58) Field of Search ............................... 607/59, 48, 49

(56) References Cited

U.S. PATENT DOCUMENTS 5,167,229 A    12/1992   Peckham et al. ............ 128/421

OTHER PUBLICATIONS

Reliability of Percutaneous Intramuscular Electrodes for Upper Extremity Functional Neuromuscular Stimulation in Adolescents with C5 Tetraplegia, Brian T. Smith et al., Arch. Phys. Med. Rehabil. vol. 75, 9/94, pp. 939–945.

"An Analysis of the Reliability of Percutaneous Intramuscular Electrodes in Upper Extremity FNS Applications", William D. Memberg et al., IEEE Transactions on Rehabilitation Engineering, vol. 1, No. 2, Jun. 1993, pp. 126–132.

"Implantation Techniques and Experience with Percutaneous Intramuscular Electrodes in the Lower Extremities", E.B. Marsolais, M.D., et al., Journal of Rehabilitation Research and Development, vol. 23, No. 3, pp. 1–8.

"Synthesis of Hand Grasp Using Functional Neuromuscular Stimulation", Kevin L. Kilgore et al., IEEE Transactions on Biomedical Engineering, vol. 36, No. 7, Jul. 1989, pp. 761–770.

*Primary Examiner*—Scott M. Getzow
(74) *Attorney, Agent, or Firm*—Fish & Richardson P.C.

(57) ABSTRACT

A functional electrical stimulation system for generating a data file storing stimulation patterns that can be provided to a stimulator is described. The system includes a host computer system for producing a data structure or data file that describes the patterns and a portable stimulator that using the data structure or data file applies electrical pulses to electrodes carried by a patient. The host computer system and the stimulator system each have a memory storing a table having control and pattern generation information with indexes into a table that separately stores electrode characterization data for each electrode used by the portable stimulator.

11 Claims, 14 Drawing Sheets

P/O 300

BREAKPOINT TABLE 308

| BKPT | NOTIF. | TIC INDEX | EVENT | CNTL | EXIT |
|---|---|---|---|---|---|
| | | | | | |
| TAG | MESSAGE | INDEX | EVENT | T OR PC | INDEX |
| | | | | | |

TIC TABLE 310

| CHANNEL NO. | PD | IPI INDEX | CURRENT | DURATION | BKPT |
|---|---|---|---|---|---|
| | | | | | |
| CHi | VALUE | INDEX | INDEX | VALUE | INDEX |
| | | | | | |

IPI TABLE 312

| CHANNEL NO | INTER-PULSE INTERVAL |
|---|---|
| | |
| CHi | VALUE |
| | |

CURRENT TABLE 314

| CHANNEL NO | AMPLITUDE |
|---|---|
| | |
| CHi | VALUE |
| | |

FRS CONDITION TABLE

| CONDITION | LEFT | RIGHT | FSR LOGIC | THRESHOLD INDEX |
|---|---|---|---|---|
|  |  |  |  |  |
| $C_i$ | VALUE | VALUE | VALUE | VALUE |
|  |  |  |  |  |

322

HALL EFFECT CONDITION TABLE

| CONDITION | RANGE | VELOCITY |
|---|---|---|
|  |  |  |
| $C_i$ | VALUE | VALUE |
|  |  |  |

324, HALL EFFECT THRESHOLD TABLE       330, BEEP TABLE

| CONDITION | LOOP COUNT | BEEP | PATTERN |
|---|---|---|---|
| $C_i$ | VALUE | VALUE |  |

326, LOOP TABLE                    334, LED TABLE

FIG. 6C

PORTABLE FUNCTIONAL ELECTRICAL STIMULATION (FES) SYSTEM FOR UPPER OR LOWER EXTREMITY APPLICATIONS

This appln is a con of Ser. No. 09/184,780 Nov. 2, 1998 U.S. Pat. No. 5,983,140 which is a con of Ser. No. 08/870,192 Jun. 6, 1997 U.S. Pat. No. 5,861,017.

BACKGROUND OF THE INVENTION

This invention relates generally to functional electrical stimulation systems and more particularly to techniques to produce stimulation patterns for functional electrical stimulation systems usable for lower and/or upper extremities.

As is known in the art, research in upper and lower extremity functional electrical systems has been ongoing for a number of years. Functional electrical stimulation uses an electronic system to generate electrical pulses that are delivered to muscles o a patient who has muscle movement impairment. The muscle movement impairment is due to some condition that causes muscle paralysis. This condition can be nerve damage c used by accident or disease. The functional electrical stimulation system produces electrical signals that can be used by the patient to control muscle movement.

Practical electrical stimulation systems require a stimulation system that is small, lightweight and portable. Such a system would to allow a subject patient to operate the system to learn to perform everyday activities. On the other hand a practical system requires sufficient versatility and power to enable practical utilization of generated electrical stimulation patterns to produce a variety of muscle movements.

Several portable systems have been described in the literature. As is known, one of the problems common to these systems is the approach used to generate the electrical signal patterns. The described systems are either built for upper or lower extremity movement but not both or either. In general, the known systems cannot handle different types of sensors. Thus, systems are designed for a particular type of sensor associated with the desired type of stimulation. Further, the approaches used to process inputs to produce stimulation waveform generally are not sufficiently robust to accommodate different sensors.

Different sensors and algorithms are necessary for each type of stimulation because the characteristics of the upper and lower extremity movements are different. Lower extremity movements can be characterized as repetitive, predictable movements, whereas upper extremity movements are more spontaneous in character. A second problem is that for practical, useful movements of muscles generally several muscles must be operates in unison or concert to produce the practical movement. Thus, in addition to providing an algorithm which allows for relatively easy generation of such produced muscle movements, it is also desirable to provide an overall system that can be adapted for upper or lower extremity stimulation or both.

SUMMARY OF THE INVENTION

In accordance with the present invention, a memory containing a data file having da a that under control of a program executed by a function al electrical stimulator (FES) system produces at least one functional electrical stimulation pattern. The pattern under control of the program provides signals that ire coupled to electrodes used by the functional electric al stimulator. The data file includes a table storing control and pattern generation information and separately storing electrode activation data for each electrode used by the portable stimulator. With such an arrangement, by storing characterization data separately from pattern data, it allows the Stimulation Pattern to be unaffected by a change in electrode characteristics, since to compensate only requires a change in the parameters of the electrode. It also allows generalized Pattern templates to be produced with most of the user specific information generated directly from Profiling sessions with a patient. This provides a unified approach to producing electrical signal patterns which takes into consideration the various complexities involved in controlling muscles.

In accordance with a further aspect of the present invention, a method of generating stimulation patterns for execution by a functional electrical stimulator system includes the steps of forming a plurality of primitive movement patterns by electrical y stimulating selected electrodes contacting a subject patient and choosing for each one of said plurality of primitive movement patterns one or more of said selected electrodes to produce the primitive movement. The method combines from the plurality of primitive movements at least one or more of the primitive movements to produce an interval pattern for each one of a plurality of desired interval movement and combines at least one or more of said interval movements to form a complex movement controllable by a user. With such an arrangement, a hierarchical approach to forming complex movements is provided. This insulates the Stimulation Pattern from the specifics of the individual electrodes profiling information and location. Thus all patterns are generated through combining of primitive movements, which are logical mappings of a desired effect (movement) to the physical stimulation required to obtain that effect, as determined during electrode profiling sessions. This allows the pattern to be unaffected by a change in electrode characteristics, since to compensate requires only a change in the parameters of the primitive movements. It also allows generalized Pattern templates to be produced with most of the user specific information generated directly from the Profiling session.

BRIEF DESCRIPTION OF THE DRAWINGS

The foregoing features of this invention will now be described in conjunction with the accompanying drawings, in which:

FIGS. 6A–6C are diagrams of a representative data file or data structure showing data tables used in the stimulator;

DESCRIPTION OF THE PREFERRED EMBODIMENT

Figure 1A:
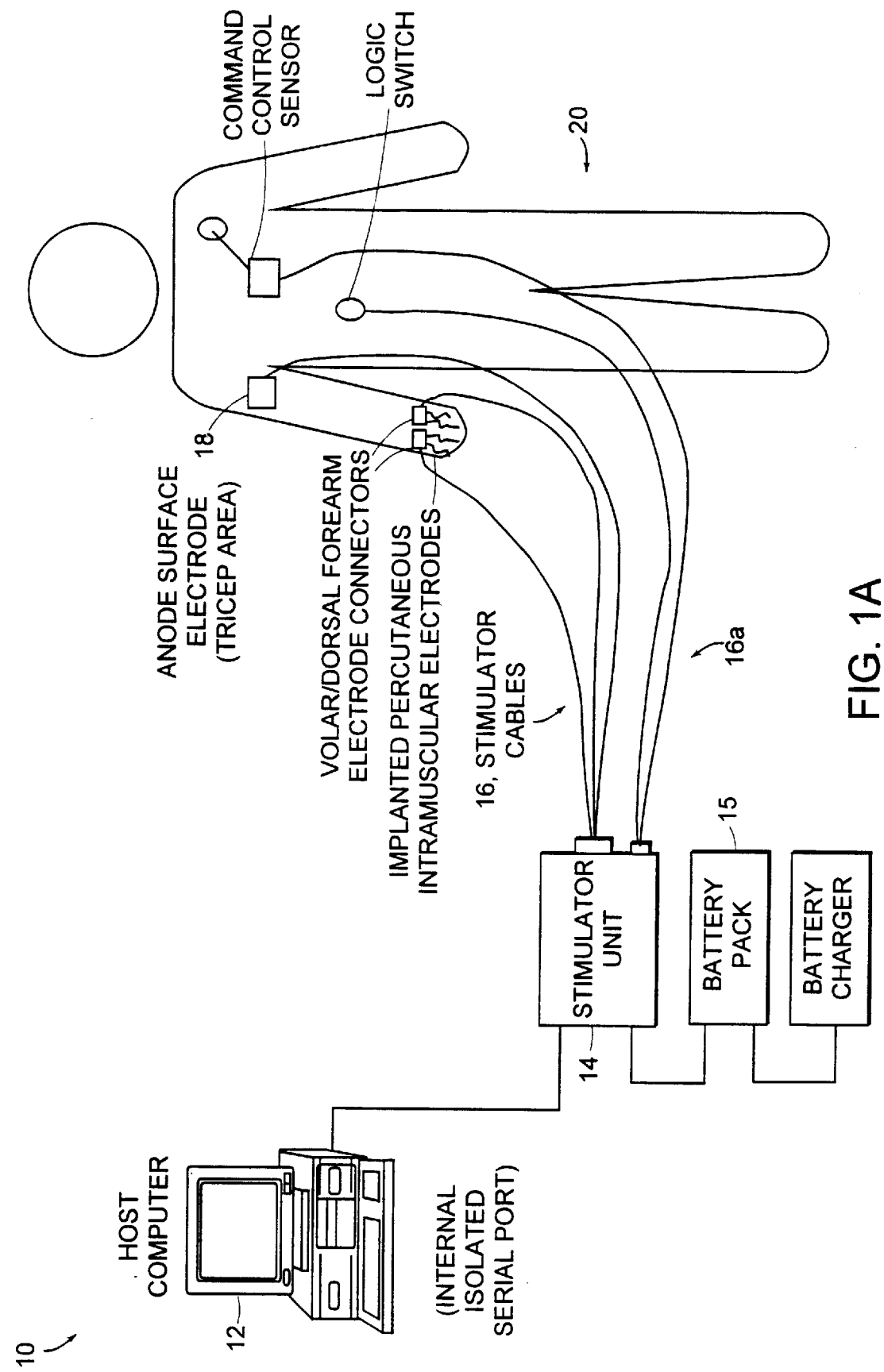
FIGS. 1A and 1B are pictorial representations of a functional electrical stimulation n system for upper body extremities (FIG. 1A) and lower body extremities (FIG. 1B).
Figure 1B:
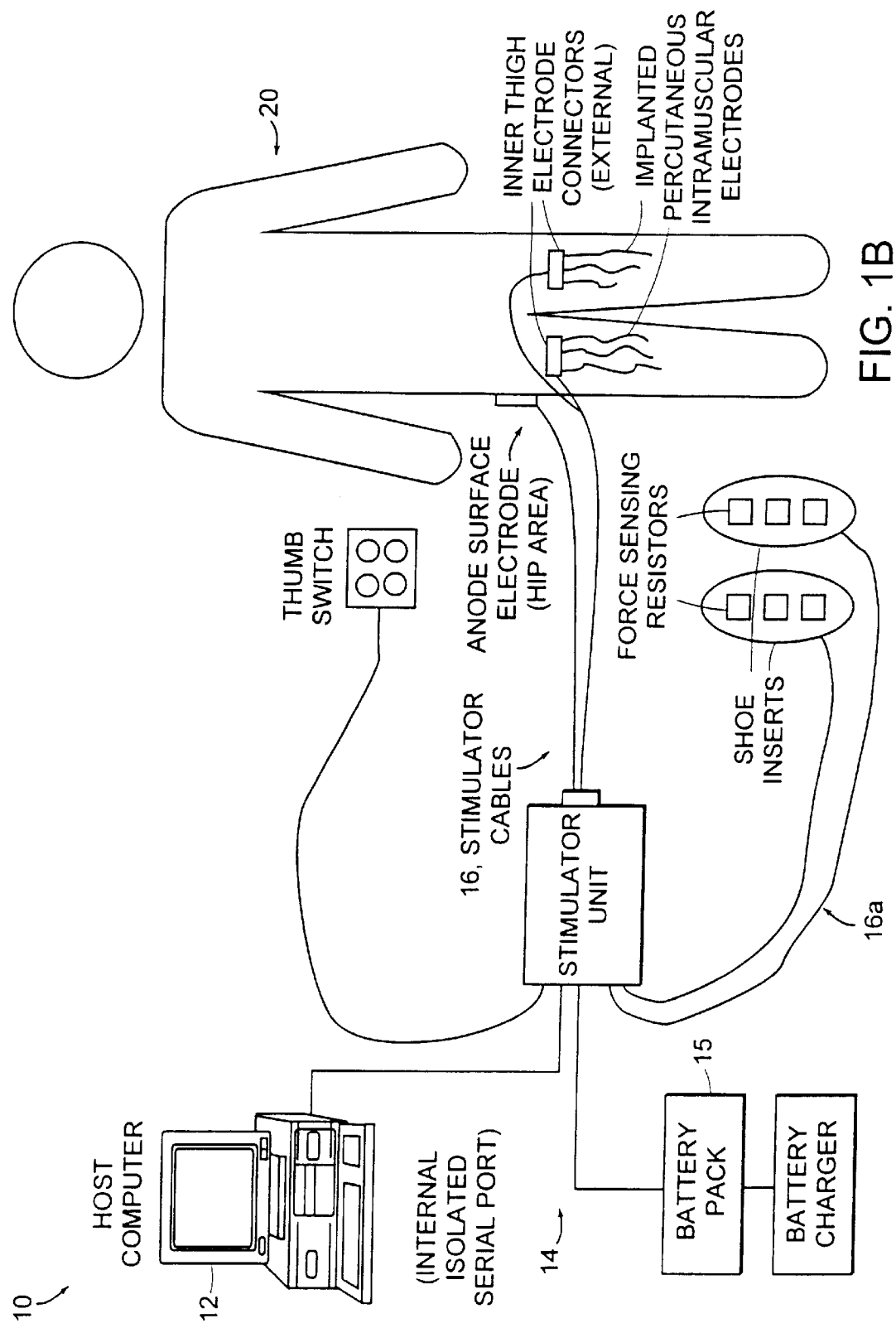

Referring now to FIGS. 1A and 1B, major system components of the functional electrical stimulation system 10 are shown pictorially interconnected to the upper and lower extremities of a human patient. In particular, the functional electrical stimulation system 10 includes a host computer 12 which executes software to generate movement patterns, as will be further described in conjunction with FIGS. 3–6. In addition to the software, the host computer 12 also stores data files which are used to provide stimulation patterns. These da files are fed to a portable stimulator unit 14. In response the portable stimulator unit 14 produces electrical signals which are coupled to the muscles of the subject patient 20 via cables 16. The cables 16 couple the stimulator to intramuscular electrodes 18 disposed on the patient upper limbs (FIG. 1A) or lower limbs (FIG. 1B). Any suitable type of muscular electrodes may be used. For example, the muscular electrodes may be of the percutaneous intramuscular electrode type which are electrodes that are implanted with a minimally invasive needle insertion procedure, as well as fully implanted electrodes or surface electrodes. Cables 16a are shown coupling various sensors (not numbered) on the human patient to the stimulator 14.

In accordance with the particular electrode type used, the stimulator unit 14 will have its circuitry adapted to suitably drive the selected electrodes. The electrodes are implanted at various locations long the limbs as shown in FIGS. 1A and 1B in a manner which would be apparent to one of skill in the art.

The stimulator unit here al so includes a portable battery pack and an outlet for a battery charger which is used to charge the battery pack In general there are two modes of operation for the functional electrical stimulation system 10. In the first mode of operation, a characterization and generation mode of operation, the host computer 10 under control of a trained operator will characterize the overall system in conjunction with a particular subject patient 20 to produce stimulation patterns for electrical signal generation. These stimulation patterns are stored as data files in the host computer system 12. After adequate generation of all stimulation patterns the data files are downloaded to the stimulator unit 14. Within the stimulator unit, the second, stand-alone mode of operation occurs. That is, under patient control the subject patient 20 can select patterns via various user interfaces to enable movement of muscles in the subject patient.

Figure 2:
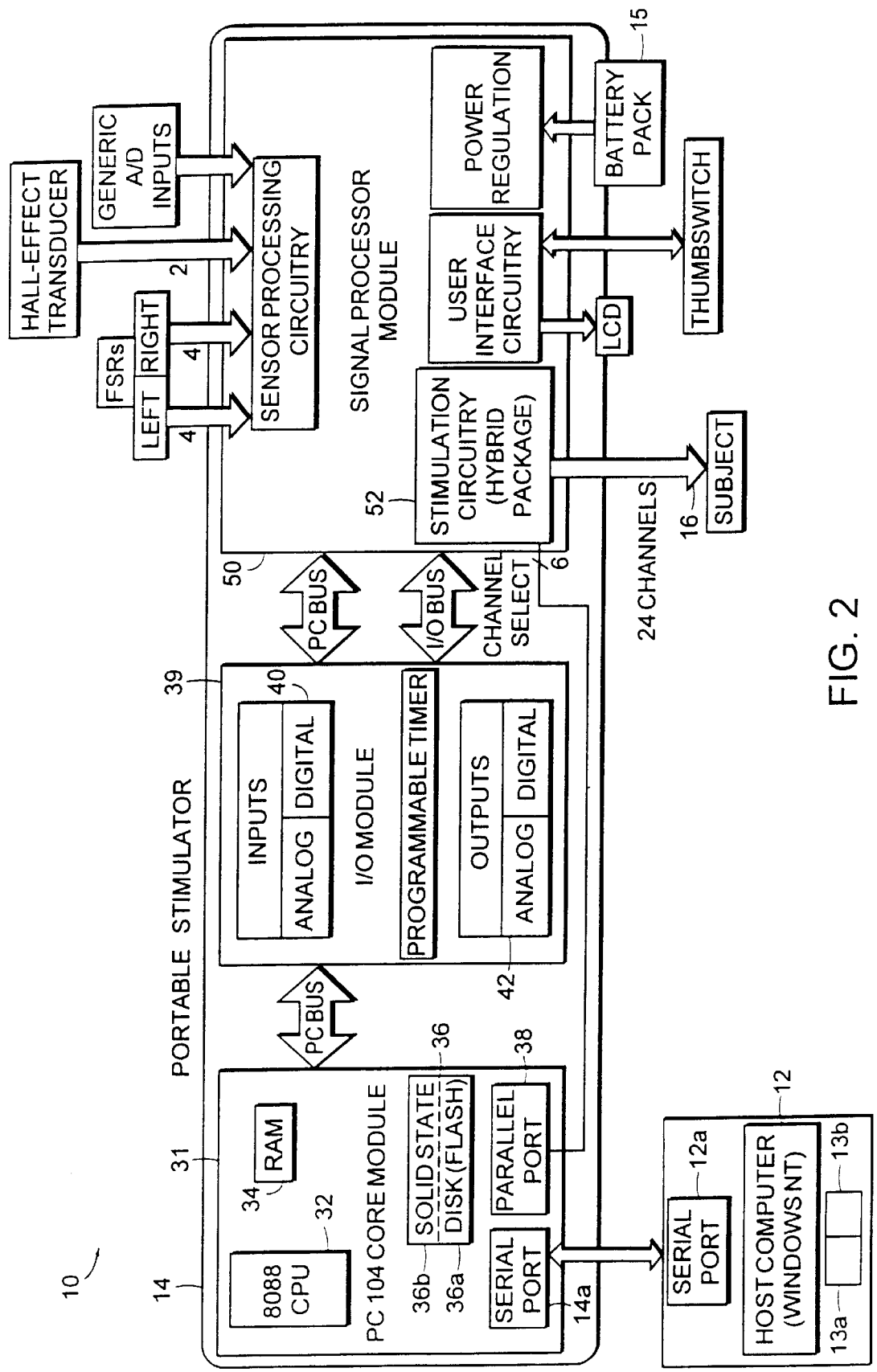
FIG. 2 is a block diagram representation of a host computer and a portable stimulator used in the functional electrical stimulation system of FIG. 1.

Referring now to FIG. 2, the functional electrical stimulation system is shown to include the host computer 12, here a PC-based computer operating under a Windows NT operating system. Other computer platforms could alternatively be used. The host has a serial port 12a which couples to a corresponding serial port 14a in the portable stimulator 14. The host computer 12 includes a software program 13a which is used to develop stimulation is patterns. The host download files 13b corresponding to the developed stimulation patterns to the portable stimulation unit 14. An example of a pattern stimulation file 13b will be described in conjunction with FIGS. 6A–6C. The stimulation pattern program comprises three portions, an electrode characterization portion, a movement development portion and a pattern generation portion. The stimulation pattern generation program 13 will be further described in conjunction with FIGS. 3–6.

The portable stimulator 14 includes an off-the-shelf single board personal computer board 31 here comprised of an eight bit CPU 32, random access memory 34, a solid state disc 36, the serial port 14a mentioned previously and a parallel port 38. The random access memory 34 is used to execute programs to produce or generate patterns for the portable stimulator; whereas, the solid state disc 36 is used to store the programs 36 a and store the pattern generation files 36b. The parallel port 38 is used to produce electrical signals which are fed through stimulation circuitry and used to produce the electrical signals which are coupled to electrodes in the subject patient. In addition to the aforementioned single board personal computer 31, the portable stimulator includes an I/O module which is coupled to the central processor 32 via a PC bus 31. PC bus 31 is also used to couple the RAM and solid state disc to the computer 32. The I/O module 39 includes provisions for analog and digital inputs as well as analog and digital outputs and is used to couple signals on a signal processor module 50 to the processor 31.

The signal processor module 50 includes the sensor circuits used to interface Hall effect transducer devices and force sensing resistors to the portable stimulator 14. The Hall-effect transducers are position transducer devices disposed on the subject patent and are used to measure joint angle for proportional control of stimulated movement. The force sensing resistors are commercially available thin film sensors having resistance changes proportional to changes in applied force. The force sensing resistors are inserted into shoes of the subject patient and are used to sense foot to floor contact during stepping. The force sensors provide reference triggers for enabling or disabling stimulation. The module 50 in addition includes stimulation circuitry 52 that produces in response to signals fed from the parallel port 38 electrical signals that are fed along the cable 16 to the subject patient. The stimulation circuitry 52 is particularly adapted or tailored for the particular electrodes which are used on the subject patient. An example of the stimulation circuitry 52 is shown in FIG. 3 for percutaneous electrodes.

Figure 3:
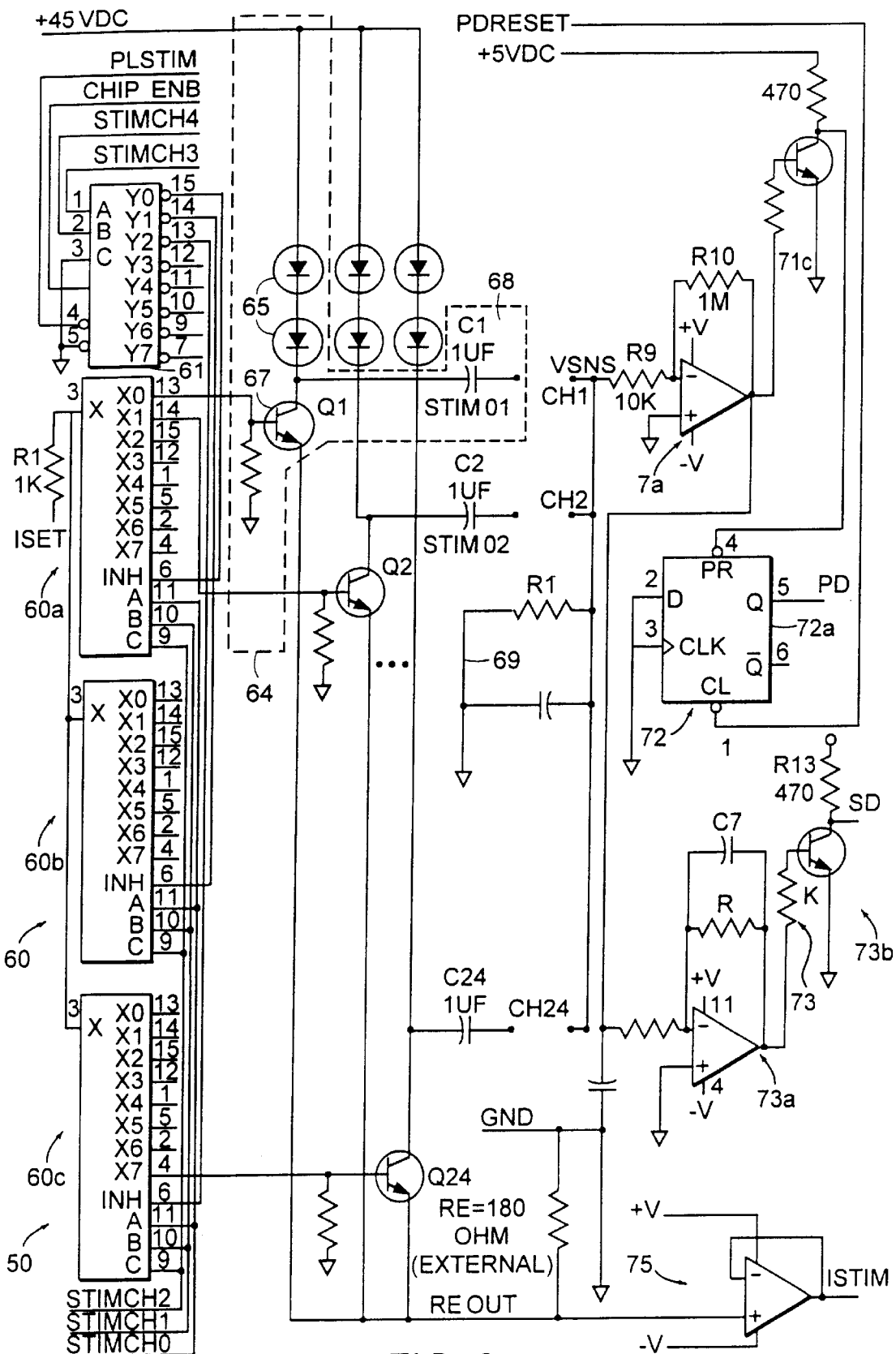
FIG. 3 is a schematic diagram of a signal processor module used to produce stimulation signals for the portable stimulator shown in FIG. 2.

Referring now to FIG. 3, the signal processor circuit 50 is shown to include a channel selector 60 comprised of three 8 channel analog multiplexers 60a to 60c and a digital decoder 61. Signals STIMCH3 and STIMCH4, PLSTIM and CHIP ENABLE are fed to the digital decoder 61 and produce as an output thereof one of three digital signals (corresponding states to 0,1 or 2 ) which act as enables to one of the three analog multiplexers 60a–60c as shown. The analog multiplexers receive as inputs, signals STIMCH0–STIMCH2 which are used to select one of eight channels in each one of said multiplexers. Signals STIMCH0–STIMCH2 and the signals from decoder 61 enable one of here twenty-four possible outputs. Thus, with PLSTIM LOW the desired channel is selected by signals TIMCH0–STIMCH2 and the selected enable signal from decoder 61.

For the desired channel selected in accordance with said signals, the signal ISET coupled to one of the 24 output channels. The signal ISET has a voltage corresponding to a desired waveform pattern. The voltage is provided from a D/A converter (FIG. 2 ). It is applied to the base of the corresponding output transistor Q1–Q24. As long as this voltage is above the base voltage of the corresponding transistor Q1 to C24, here 0.85 volts, the corresponding transistor is turned on causing the associated one of the capacitors C1 to C24 at the output stage of each one of the said transistors Q1 to Q24 to discharge. The stimulation current is then produced and can be calculated by the following equation based on the voltage level IST:

$$I_{simulation} = ((IST - V_{BE})/R_g) - 0.5$$

where RE is a 180 ohm emitter resistor. When PLSTIM returns to a higher level, the corresponding transistor in the channel is turned off since the base is pulled down by a 100

Kohm resistor. The corresponding stimulation capacitor C1 to C24 is then recharged at a rate not greater than 0.5 milliamps as limited b the diodes D1–D48 in the collector circuit of the transistor.

The signal processor circuit 50 in addition includes three circuits which are used to monitor the stimulation status. An operational amplifier 71a is used to sense the pulse which occurs in the select ed one of the channels CH1–CH24 and is used as an input to the pulse detection 72, short capacitor detection 73 and pulse sense circuits 75. The operational amplifier 71a amplifies the pulse signal at node VSNS by a value corresponding to the gain of the amplifier 71a, here −100. If the amplified output value of the voltage VSNS is greater than VBE of the transistor 71c, then the base of the transistor kill turn on triggering the D-Flip Flop 72a causing the pulse being sent signal "PD" to assert. This signal is fed to the CPU in the stimulator 14 to indicate that the pulse was in fact,sent. The signal PDRESET provided from the CPU In response to PD resets the flip flop 72a and causes signal PD to deassert in anticipation of the next stimulation pulse. A resistor R1 and capacitance C1 are disposes to provide a low pass filter 69 between VSNS and ground. The lowpass filter 69 prevents detection of low duration or low level signals.

A shorted capacitor condition circuit 73 detects a constant current flow through the resistor R1 when there is no stimulation pulse. Thus, the potential at VSNS is also used to detect a shorted capacitance that is proportional to the current. For this circuit, the voltage is amplified in two stages. The first stage corresponds to stage 71a and the second stage correspond to a second operational amplifier stage 73a. If the potential at VSNS is greater than the base emitter voltage a the transistor 73b, the transistor will turn on causing SD to go low. This condition occurs if the leakage current is greater than 0.02 milliamps.

The third circuit 75 is a circuit used to measure the output pulse. The signal ISTIM (stimulator current) is a buffered reading of RE_OUT to check if the programmed current matches the actual current. The value of ISTIM is only meaningful during stimulation. It is fed to an A/D converter and digitized to produce a digital signal which can be compared against the corresponding digital signal used to produce ISTIM voltage level.

Figure 4:
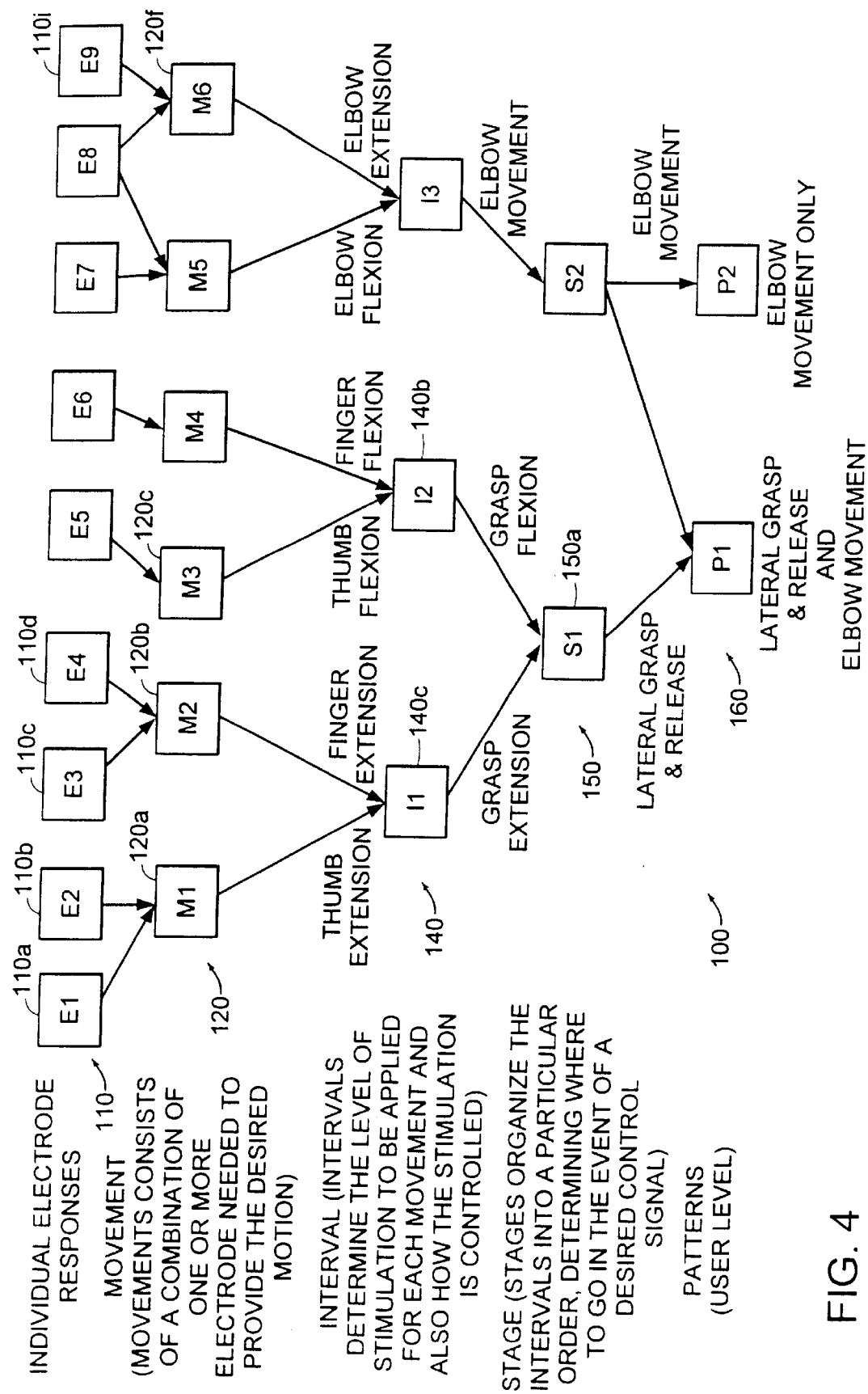
FIG. 4 is a flow chart showing the major steps required in generating a movement pattern at the user level.

Referring now to FIG. 4, a process 100 used to generate movement patterns for a subject patient is shown. The process 100 is executed in the host system 12 under control of a trained operator.

At a first or initial level the host computer system 12 is used to characterize each i individual electrode response 110a to 110i through electrode profiling. Electrode profiling provides a technique to describe the electrical parameters needed to stimulate a given electrode to produce a desired muscular response. Each electrode in every patient is profiled for this purpose. Each electrode is assigned a unique number used for identification. This number is mapped to the channel to which the electrode is connected. This allows the electrode's characteristics to be portable and not associated with any specific channel The electrode is profiled to provide the information needed to accurately describe its characteristics.

The first step in profiling an electrode is to select an appropriate amplitude and frequency (NOTE: When these parameters are adjusted, the profile information is reset. Also these will be the default parameters for the given electrode). Once appropriate parameters are established, the affected muscles can be determined. Up to three muscle/movement pairs can be recorded with the following information:

| | |
|---|---|
| 0% | Threshold pulse duration |
| 100% | Saturation pulse duration |
| Force/ Strength of Muscle | Scaled from 0 (no response) to 5 (Normal) (Manual Muscle Test Scale) |
| Length Dependency | Scaled from 0 (non-functional) to 2 (Functional) |

A history of the information is recorded as the electrode is profiled more than once to allow the operator to use the information from a past profiling session if necessary. The values of frequency and amplitude are stored in tables IPI and Current, as will be described in conjunction with FIG. 6.

It is generally necessary to characterize the electrode responses for each implant electrode to determine whether or not multiple electrodes are required to generate a particular muscle movement. Often with percutaneous electrodes multiple electrodes are required to generate sufficient force to produce sufficient muscle movement. The force generated by the muscle is dependent upon several variables including, most notably, electrode position. The technique of needle insertion of percutaneous intramuscular electrodes is a somewhat inexact science. Often more than one electrode is necessary to generate sufficient force to produce sufficient movement of the muscle.

After each of the characteristics of the electrodes have been ascertained, primitive movements are developed. Desired, primitive movements are selected and generated as a result of the combination of one or more electrodes needed to provide a desired motion. This is an iterative process in which electrical stimulus is provided to one or a group of electrodes and the reaction, i.e., physical movement of the muscle in the subject patient is observed and recorded in the host computer. In this manner the requisite number of electrodes and weights for each of the selected electrodes are determined. Thus, as shown in FIG. 4, for the thumb extension movement 120a M1, two individual electrode responses from electrodes 110a and 110b are weighted and combined to produce the required electrical stimulation for the desired thumb extension movement. Similarly, for each one of the other movements 120b–120f different combinations of electrodes and weights are selected and assigned to the electrodes. Thus, finger extension movement 120c is provided by weighting responses of electrodes 110c and 110d and so forth.

Figure 5:
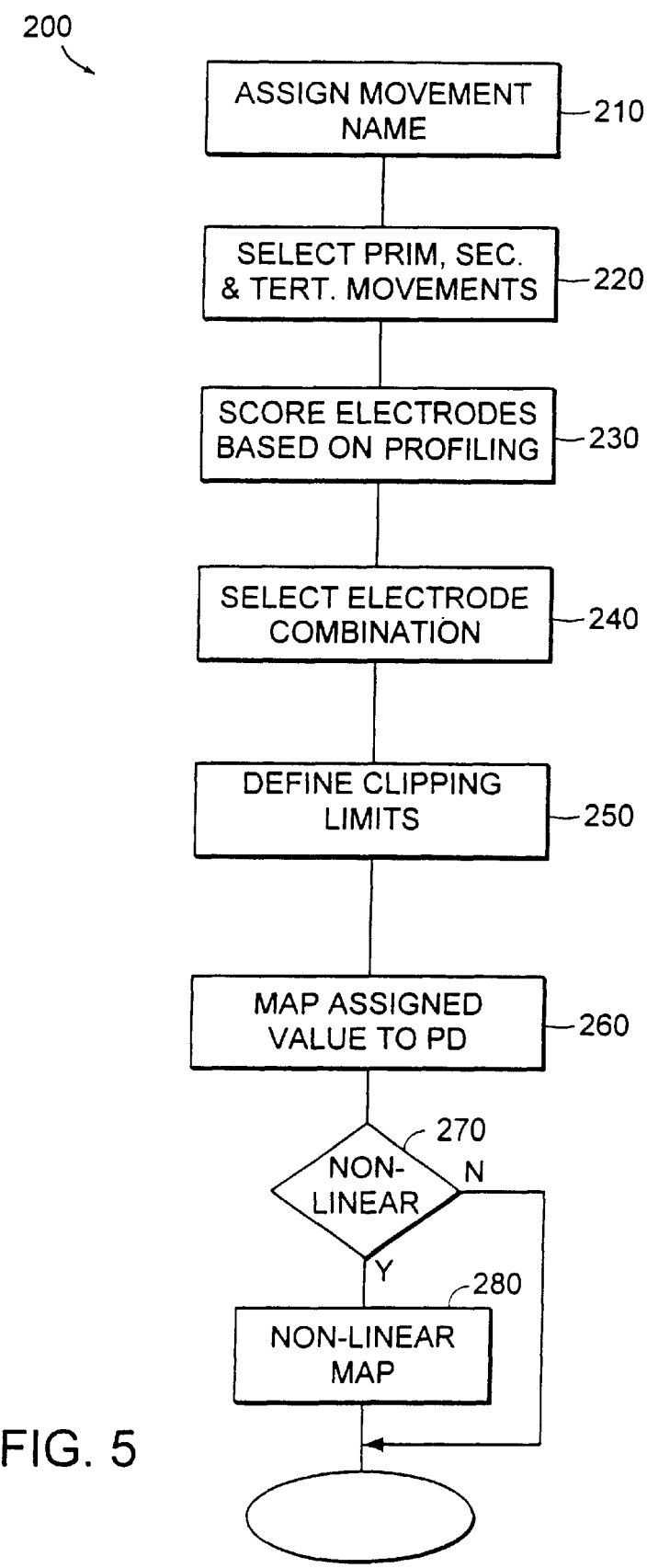
FIG. 5 is a flow chart of a technique to form primitive movements.

Referring now to FIG. 5, an electrode to primitive movement mapping technique is shown. To insulate the Stimulation Pattern from the specifics of the individual electrodes profiling information and location, all patterns operate through primitive movements, which are logical mappings of a desired effect (movement) to the physical stimulation required to obtain that effect, as determined during Electrode Profiling sessions. This layer of abstraction allows the Pattern to be unaffected by a change in electrode characteristics, since to compensate requires only a change in the parameters of the Primitive Movements. It also allows generalized Pattern templates to be produced with most of the user specific information generated directly from the Profiling session.

A Primitive Movement is assigned a unique name (step 210 ) generally descriptive of it function. Each Primitive Movement can specify up to three desired movements, in order or priority, as its Primary, Secondary and Tertiary movement. This will provide a list of electrodes that produce the specified movements (step 220 ). These electrodes are sorted, from "best" to "worst", according to their appropriateness for the g given movements selected, based on the Electrode Profiling. The purpose of identifying primary, secondary end tertiary movements is that certain muscles can produce several movements from a single stimulation because the muscle crosses one or more joints in the body. For certain complex movements, the secondary and/or tertiary movements can be beneficial and thus used in generating the movement. For other complex movements, the secondary and tertiary movements hinder the desired complex movement. With the latter case, an attempt is made to compensate for these secondary and tertiary movements.

Therefore, any combination of some or all of the resulting electrodes may be used with the default being that only the "best" electrode is enabled and all others are disabled (step 240 ). Each electrode can have specified the Minimum and Maximum, artificial clipping limits that specify the range that the user is permitted to adjust the pulse duration in. These values default to the 0% (Minimum) and 100% (Maximum) of the Primary Primitive Movement of the electrode.

Because with percutaneous intramuscular stimulation it is common to use several electrodes in combination in order to generate a singular stimulation movement, for example, a knee extension or a finger flexure, a movement development window is designed to effectively determine the combined effects of several electrodes before combining different movements. The user can select primary, secondary and tertiary movements from a database of muscles and associated movements. Based on the selection, the computer chooses the best electrodes using a weighted combination of the muscle force and length dependency scores determined during electrode characterization. The operator can activate the chosen electrodes simultaneously to observe the combined effects. In order to have a consistent interface between Patterns and Primitive Movements, all Patterns refer to the Primitive Movement as having a value between 0 and 100 inclusively (NOTE: A value of 0 corresponds to a pulse duration of 0, no stimulation, for all electrodes) (step 260). These values are mapped to electrode pulse durations. The default mapping of Indexes to pulse durations is a ramp function from the 0% to the 100% of the Primary Movement. The starting point and end point of the ramp can be modified to any value in the range specified by the Maximum and Minimum.

Since the response of many electrodes is nonlinear with pulse duration, a mechanism (step 270 ) to allow a piecewise linear mapping is provided. Up to 6 sub-ramps are permitted per electrode allowing a variety of waveform shapes. These sub-ramps can begin n and end at any index and specify any pulse duration within the acceptable range. This piece-wise mapping of Movement Indexes to multiple electrode pulse durations allows the Movements to perform complex functions, if so desired The movement is tested until the desired electrode combination and pulse width mapping is achieved.

After suitable movements have been achieved, a three step hierarchial approach is used to combine the Primitive Movements to enable more complex control of muscles and to enable move complex operations. Stimulation patterns are generated in a hierarchical configuration, broken down into three separate levels. These are, from lowest complexity to highest, Intervals, Stages, and Patterns. By using such an approach, it is possible to develop a database of movements and to combine Primitive Movements in the database in different combinations to achieve new complex movement patterns. This can be achieved rather economically since all the initial characterization of the Primitive Movements is already performed. Thus, it is merely necessary to combine the primitive movements to achieve the more complex movements.

The first level of the hierarchical process is the interval level. At this level, intervals are developed which include a combination of movements as shown at 140. Thus, for example, the interval "grasp extension" is a combination of a "thumb extension" movement 120*a* and a "finger extensions" movement 120*b*. Defined within the interval is, in addition to the movements is the type of control to be used; that is, whether the control is a time based control or a proportional based control. Further, the duration of the time interval or a proportional signal based on the control selected are also determined. In addition, any break points or branching points to alter, stop or hold stimulation movement are selected. Branching conditions include reaching a threshold level of the force sensor resistors or a threshold level of the Hall-effect transducers, hitting a button on a thumb switch unit or a loop option to automatically repeat the interval.

Intervals provide the lowest level of control, containing the information for stimulation, user notification, and branching conditions. This information is stored in the following tables: Tics and breakpoint. The Tic contains the basic information for stimulation. The contents of the Tic table describe pulse-shape parameters. The Tic table contains, for each channel, the Pulse Duration (0–255 uS.), the Inter Pulse Interval (IPI, 1–1023 mS.), and the Amplitude ( 0.0–20.0 mA.). Also in the Tic is the information about how long to star at the Tic and what action, if any, to take during the Tic (see Breakpoint).

There are currently two methods of controlling stimulation; Timed and Proportional control. Each of these two types requires the same information in the other fields, however, the information is interpreted differently. The difference between the two control methods is the default destination when the Tic is completed. In Timed control, the Tic simply proceeds to the next Tic. In Proportional control the next Tic is determined by a Control Signal. An external signal ranging from 0 to 100 is mapped to a value between 0 and 399 and used to index the next Tic. The external signal is generated from the Hall Effect sensors or from the force reaction of another muscle. The duration of the interval specifies the overall length that the interval takes to execute. For Timed Intervals, this is a value in mS which also determines the number of Tics in the Interval. For Proportional Intervals, this value is between 1 and 100 and determines the percent of the command range that this interval occupies. The Breakpoint contains the information that determines the user notification and the branching condition. The user notification is a message displayed on the LCD of up to 9 characters, a programmable Beep Pattern, and a programmable blink pattern on the Thumbswitch LEDs. The branching condition can be one of the following:

| | |
|---|---|
| GO button | met when the GO button is depressed during the Breakpoint |
| FSR trigger pattern | met when any logical combination of above or below programmed thresholds |
| Hall effect | met when normalized velocity meets specified conditions |
| Loop #N times | met first #N times, then not met all times after that |

The branching condition can be triggered at any time during the interval. For a Timed Interval, the Breakpoint is valid during the first Tic of the Interval, which can be of a programmable duration. For Proportional Interval, the Breakpoint can be valid for any desired percentage of the first part of the entire Interval. The option exists in the Breakpoint to disable the ability to have an emergency exit.

As shown in FIG. 4, at the next level a stage 150 is developed which combines a group of intervals to produce a more complex movement. The stage level integrates control and generation information for the selected intervals. A Stage can contain only Intervals with the same control type, either proportional or timed. A Stage also controls the branching from one Interval to the next. When the Breakpoint of an Interval is completed, depending on the exiting condition, the Stage can branch to either another Interval in the Stage or to a special destination. The exiting conditions of the Breakpoint can be one of the following three:

| Default | Occurs when wait time has expired and no other condition met. (Not valid for PC) |
| Event | Occurs when the Breakpoint condition is met |
| Exit | Occurs when the Exit condition (EXIT Button) is met |

Each of these conditions can have their own destination of any Interval in the Stage or one of the following special destinations:

| Continue | Continues to the next Tic (Timed only) |
| Stage Next | Goes to destination specified by Pattern |
| Stage Branch | Goes to destination specified by Pattern |
| Stage Exit | Goes to destination specified by Pattern |
| Next Interval | Goes to the next Interval in the Stage |
| Previous Interval | Goes to the previous Interval in the Stage |
| Stim Unlock | Unlocks Stim |

For example, as shown in FIG. 4, the "grasp extension" interval 140 a can be combined with the "grasp flexion" interval 140b to produce a lateral grasp and release movement 150a. A stage controls both the interval sequence as well as branching conditions between intervals.

The next level in the hierarchy is the Pattern. At the highest level, one or more stages are brought together to represent a pattern as shown in level 160. This is the level at which the user chooses and controls stimulation movements. For example, a pattern can be several stages such as lateral pinch and elbow extension or standing and sidestepping. The Pattern is similar in structure to the Stage. A Pattern contains a group of Stages and the branching relationship between them. The Branching conditions can be one of the following three:

| Next | Occurs when Stage Next destination occurs in Stage |
| Branch | Occurs when Stage Branch destination occurs in Stage |
| Exit | Occurs when Stage Exit destination occurs in Stage |

The destination of each of the conditions can be any of the Stages in the Pattern or one of the following Special Destinations:

| Menu-Stim On | Returns to the Menu leaving Stim On |
| Menu-Stim Off | Returns to the Menu turning Stim Off |
| Next Stage | Goes to the next Stage in the Pattern |
| Previous Stage | Goes to the previous Stage in the Pattern |

Once a stimulation pattern is designed, the program produces a simulation parameter table (as will be described in FIGS. 6A to 6C) that contains all the information necessary for the stimulator to execute the pattern. The stimulation pattern table is downloaded to the solid state disc 36 (stored as file 36b) in the stimulation unit 14 via the serial interface. Typically several patterns for functional use and stimulation exercise are developed and transferred to the stimulator 14. Pattern choices are displayed on an LCD and chosen via thumb switches or Hall effect transducers as appropriate for the pattern and the patient.

The program resident in the stimulator executes a stimulation pattern retrieved from a stimulation parameter table in accordance with that desired by the thumbswitches or the Hall effect sensors. The program in the stimulator schedules and executes stimulation pulses for each channel, samples and processes control signal data and performs user notification via the LED display on the Thumbswitch, the LCD display and audio tones. On command from the stimulation parameter table, the program will also store data such as the control signal system mode, time and data views and pattern used in approximately 1 megabyte of unused solid storage disk space.

Once the patterns have been produced, Menus can be produced to control which Patterns and functions are accessible to the user of the stimulator. Menus can be controlled either with the Thumbswitch or by the Hall Effect Transducer. Three different kinds of menu items can be added to each Menu:

| Menu | Other Menus (Sub-Menus) |
| Patterns | User programmed Patterns |
| Functions | Predefined functions and procedures |

Upon system power up, the Menu Main Menu will become active, so any desired Menu, Pattern or Function must either be in this Menu or in one of the Menu Branches originating in Main Menu.

Figure 6A:
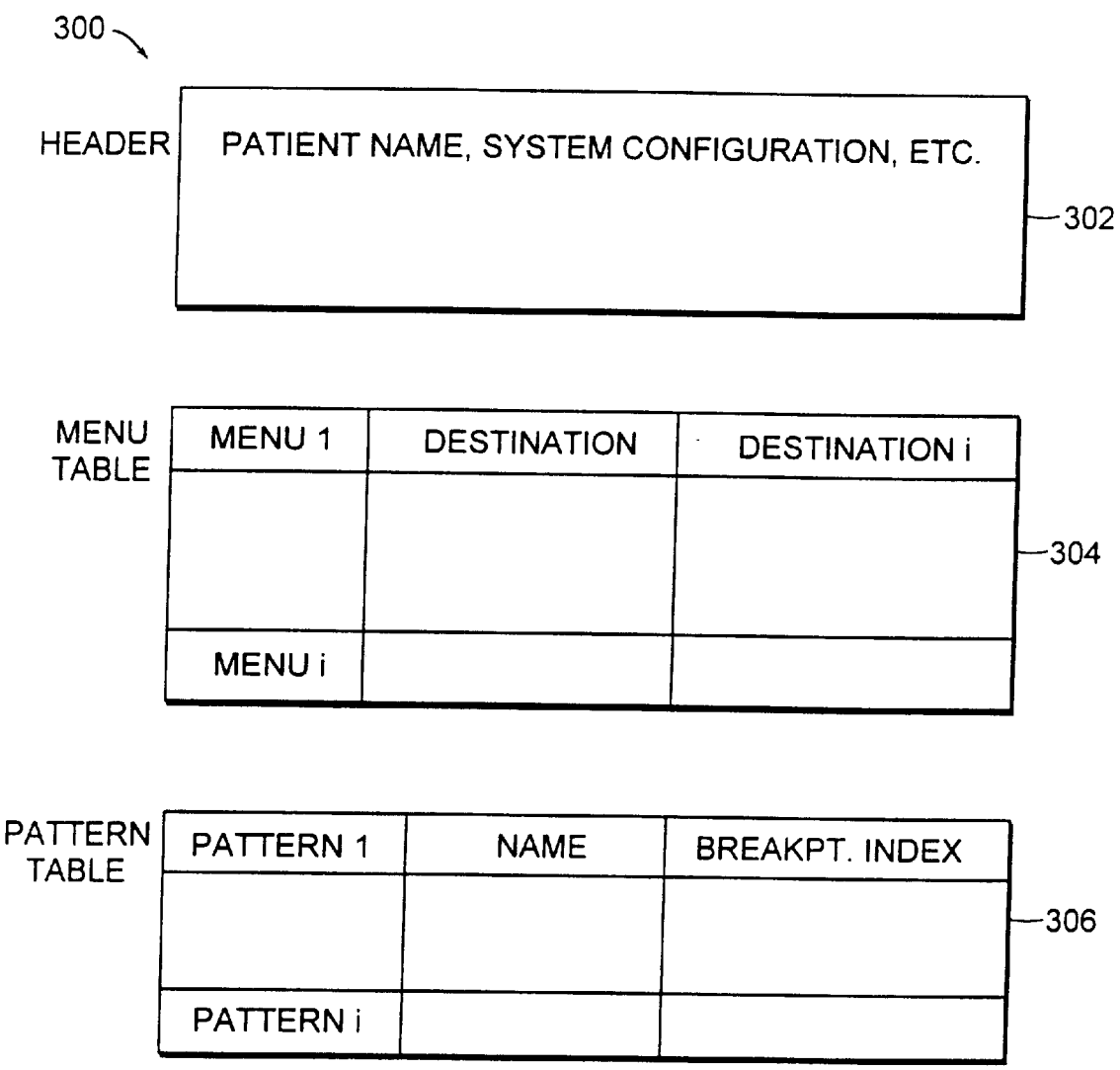

Referring now to FIGS. 6A–6C, an illustrative pattern stimulation file 13b produced by the host system 12 for use in the portable stimulator system 14 is shown to include a header file 302. The header file 302 contains general information concerning the configuration of the system and the patient who is using the system. After the header file are one or more menu tables 304. Each of the menu tables contains all of the information for a menu system which allows a user to navigate through the system and perform desired tasks. Each menu allows the user to select one of several possible Destinations. In addition to Destination information, the menu also contains information regarding how the menu is navigated, that is, by Thumbswitch or Hall Effect Transducer. Each Destination allows a user to select one of several possible options. The Destination contains information on the type of destination, current menu, pattern and function, as well as an index into a table for each of the types.

The next table is a pattern table 306 which contains a list of all user selectable patterns. Each user selectable pattern 306a–306i contains a field corresponding to the name of the pattern and an index into a Breakpoint table which provides the starting point for the pattern.

The Breakpoint table 308 contains a listing of all of the Breakpoints. Each Breakpoint contains several fields which provide special information used during stimulation to control the flow of the Pattern. Each Breakpoint includes a notification field which contains a <message>which is used to produce user feedback through the visual display and LED as well as auditory beep sounds. The next field is a Tic index which contains an index into Tic tables. The Tic table 310 determines the stimulation levels. The next field is an event field which contains information which permits the system to handle a special event. The types of events supported include operations triggered by assertion of a GO button, force sensing resistors (FSR), Hall Effect Transducers and a LOOP option. Since there are in general more than one condition for each of the types, an index into the desired type is also provided. If a special event occurs, then the Pattern branches to the event Breakpoint index specified in the table.

If no event is desired or if an event does not occur then the control type specifies the type of control to be performed on the pattern. Two types of control are provided, time control and proportional control and are specified in control field. The control type also specifies the Destination that the CPU will go to after the control operation is executed. The next field in the Breakpoint table is an EXIT condition field which is used to handle emergency condition such, for example, if the user presses the EXIT button. This field contains the EXIT Breakpoint index which will control where the patterned branches should be.

The next table in the file 300 is the Tic table 310. The Tic table contains data used to provide pulse shapes and duration for the stimulation pulses. The Tic table contains a list of all Tics, inter-pulse intervals and current amplitude tables. The Tics contain the information required for stimulation. This information includes the pulse duration in microseconds stored in field 311a for each channel, an index into the IPI table in field 311b and an index into the current tables in field 311c. The IPI table 312 and current amplitude tables 314 as shown contain respectively the inter-pulsed interval in milliseconds for each of the channels and the current table contains a current level or amplitude for each of the channels. These tables are populated independently of the pattern generation process. They are populated during the electrode characterization process and thus permit changes in electrode characterization to have a minimal effect on pattern generation. The IPI table 312 and the current table 314 are shown having an index corresponding to channel number and a value associated with the index.

As shown in FIG. 6C, the file further includes force sensing resistor condition table 320, Hall Effect condition table 322, Hall Effect threshold Table, 324, Loop tables 326, Beep table 330 and LED table 334.

For each force sensing resistor, the FSR table contain fields corresponding to left condition, right condition, FSR logic and a threshold index. The FSR Condition Table contains a list of all of the FSR Conditions and FSR Thresholds. FSR Condition fields contain information to describe a Breakpoint Event condition for the FSRs which, if met, triggers the branch in the Breakpoint. The Left Condition field contains a Truth Table for the four FSRs on the Left foot. This allows the result for any combination of On/Off (a total of 16 possibilities) to result in a triggering condition. The Right Condition field contained the Truth Table for the four FSRs on the Right foot. This allows the result for any combination of On/Off (a total of 16 possibilities) to result in a triggering condition. The FSR Logic field indicates what combination of the Left and Right Conditions will result in the triggering being met. These conditions include:

Left Only
Right Only
Left And Right
Left Or Right

The Threshold Index field contains an index into the FSR Threshold Table describing which table of Thresholds is to be used for the FSRs to be considered On or Off. The FSR Threshold Table contains an array of Thresholds for each of the FSRs, above which the FSR is considered On, below which the FSR is considered Off.

For the HALL Effect condition table 322, each Hall condition contains a field corresponding to range and a field corresponding to velocity. The Hall Condition Table contains a list of all of the Hall Conditions and Hall Thresholds. The Hall Condition field contains information to describe a Breakpoint Event condition for the Hall Effect sensor which, if met, triggers the branch in the Breakpoint. The Range field describes a minimum distance the Hall Effect sensor must travel in a specified amount of time in order for the Hall Condition to be met. In the Velocity field, if the Range condition is met, then the Velocity of the Hall Effect sensor must be above this value and also below a fixed limit. If these three conditions are true, then the triggering condition is met. The Hall Threshold table 324 specifies the number of levels of the Hall Effect sensor's range. This is currently used to control accessing Menus and for Proportional Control Indexing.

The Loop table 326 contains a stored value for each Loop count condition. The Loop Table contains information to describe a Breakpoint Event condition to branch to the same Breakpoint a specified number of times. The Loop Count indicates the number of times to repeat the Breakpoint branch. The triggering condition is met for Loop Count times, then it is not met again. Similarly, the Beep table and the LED tables have stored values for each Beep pattern and LED pattern, respectively. The LED Table contains an array of LED Patterns. These are accessed by the Breakpoint Notification field. The LED Pattern describes a blinking pattern for the LEDs and contains the information to describe an On/Off pattern, the frequency of switching, and the total duration of the pattern. The Beep Table contains an array of Beep Patterns. These are accessed by the Breakpoint Notification field. The Beep Pattern describes a beeping pattern for the Beeper and contains the information to describe an On/Off pattern, the frequency of switching, and the total duration of the pattern.

Functions are not contained in the pattern stimulation file 13b. The functions are predefined and built into the program. The Destination field is a way of accessing these Functions.

Figure 7:
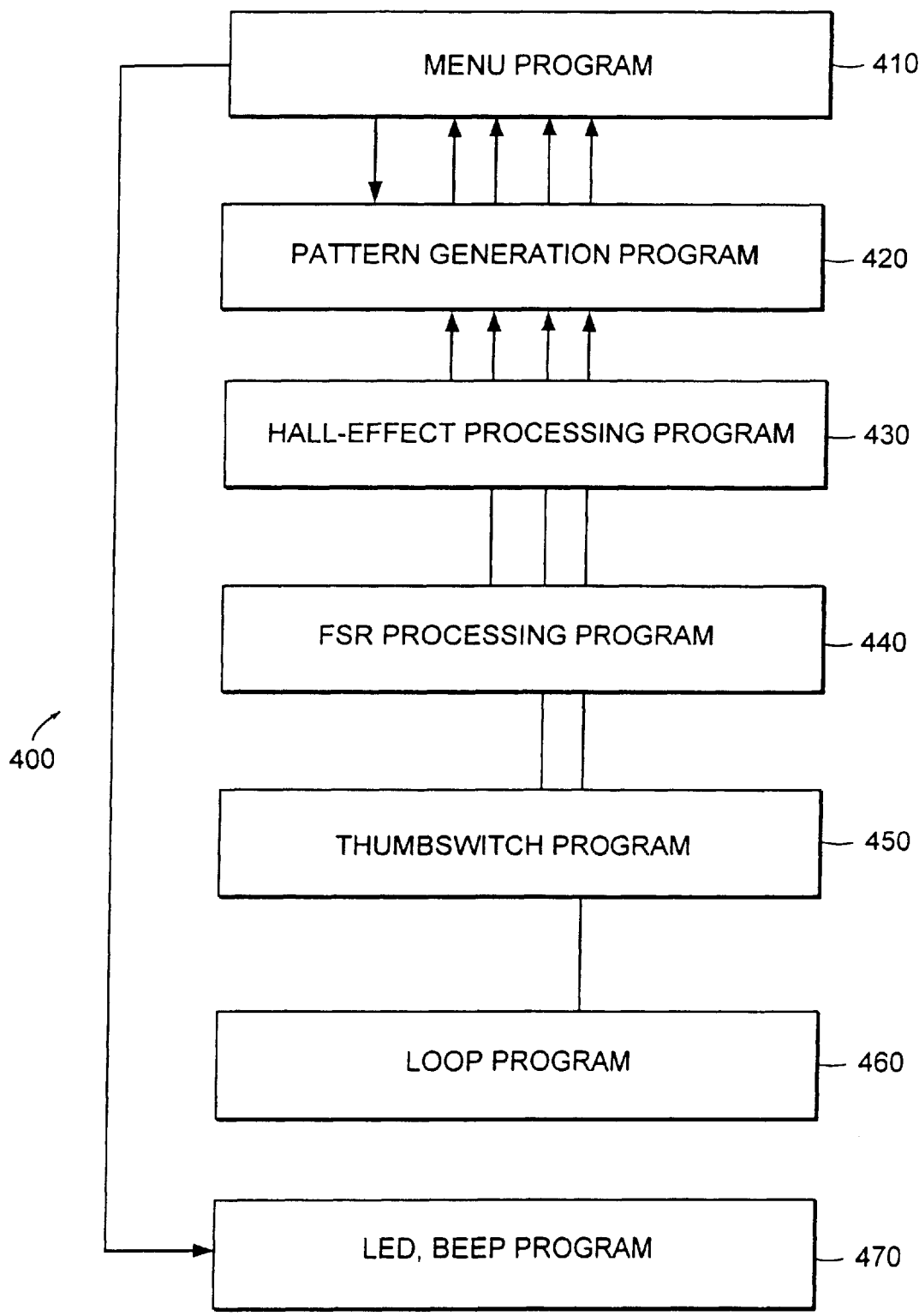
FIG. 7 is a flow chart showing steps in using the dat structure of FIGS. 6A–6C to produce stimulation signals.

Referring now to FIG. 7, the major routines in a software program 400 executed on the portable stimulator 14 are shown. The program 400 includes a menu processing program 410 which responsive to inputs from user control devices provides menu screens (not shown) to enable the user to step through the various features of the portable stimulator 14. The menu program also provides a pattern index to a pattern generation program 420 in accordance with a pattern selected by the user.

Figure 8A:
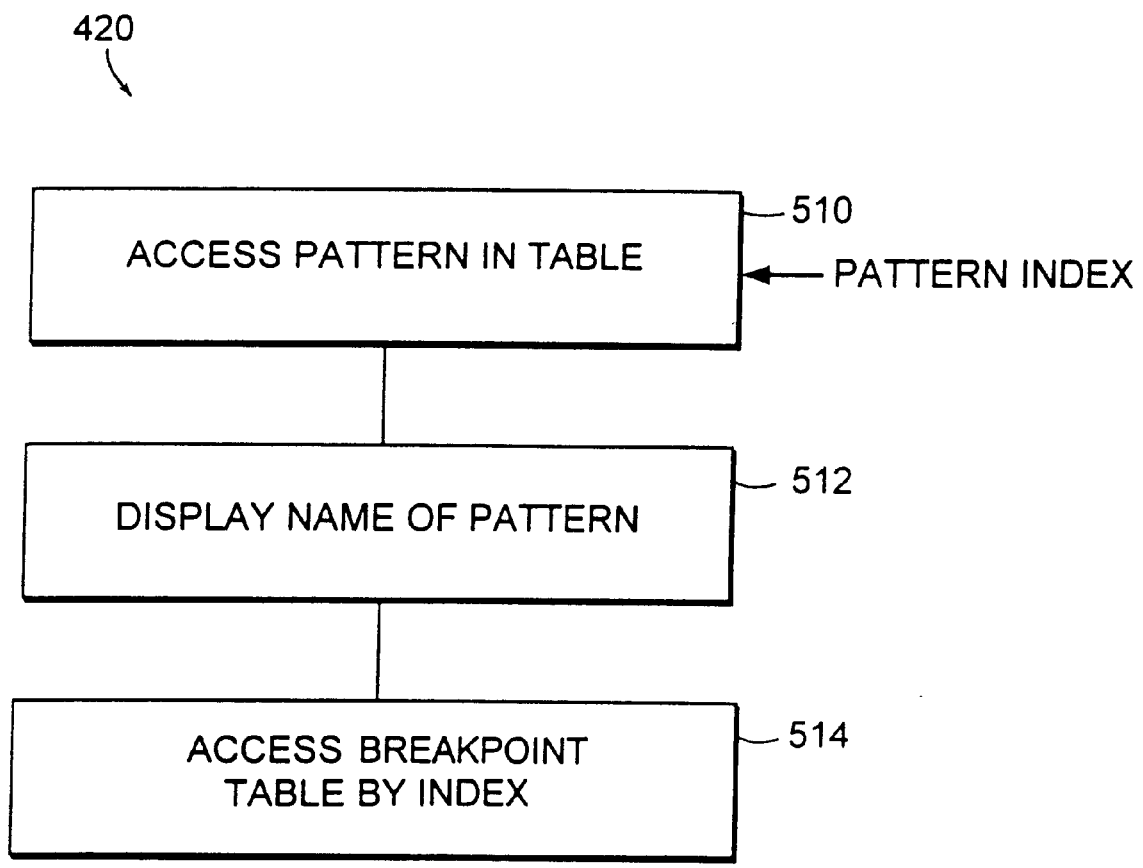
FIGS. 8A to 8D are flow charts showing steps used in generating stimulation patterns.
Figure 8B:
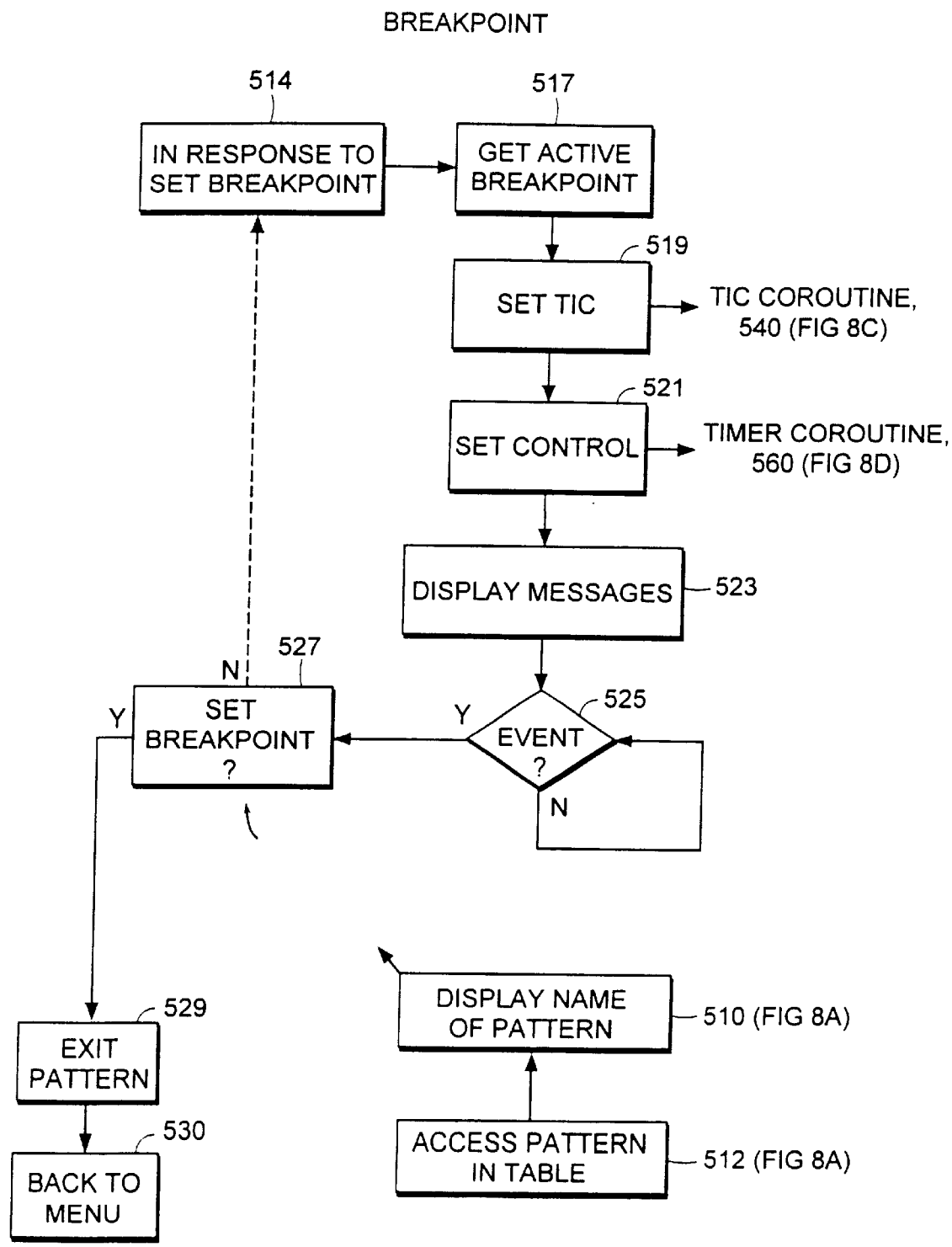

Therefore, the software program 400 also includes the pattern generation program 420 (which will be further described in conjunction with FIGS. 8A and 8B. The pattern generation program produces the stimulation signals on the electrodes 18 coupled to the subject patient in accordance with inputs provided by sensors disposed on the patient. The software program 400 also includes Hall Effect processing program 430, force sensing resistors (FSR) program 440, Thumbswitch program 450 and loop program 460. These programs process inputs to the menu program 410 for display in the menu and the pattern generation program 420 to control generation of stimulation patterns.

The software program also includes an LED, beep program 470 which is used to control in conjunction with the menu program 410 visual/audio messages to the user.

Referring now to FIGS. 8A–8D, the pattern generation program 420 which is executed in the stimulator 14 is shown to include step 510 which is used to access a particular stimulation pattern in the pattern table 306 (FIG. 6A). The pattern table is indexed via the pattern index provided from the menu program 410 (FIG. 7). In step 512, the name of the pattern is displayed (via processing by the menu program and LED/beep program). At step 514, the program 420 accesses the Breakpoint table by the index provided from the pattern table.

Referring now in particular to FIG. 8B, the pattern generation program 420 uses information in the Breakpoint table as follows:

In response to setting a breakpoint at step 515, the software retrieves the active breakpoint at step 517 and sets the Tic index at step 519. The Tic index is used to index into the Tic table using the Tic routine 540 as will be described in conjunction with FIG. 8C. The Breakpoint is also used to set the control index at step 521 which will use the timer routine 560 (FIG. 8D). The Breakpoint routine displays messages in the Breakpoint table at the Breakpoint index at step 523. At this point if an event is indicated at step 525, the software will branch to check if a breakpoint has been set at step 527 with new data provided from steps 510 and 512 as shown. Thereafter, it will exit at step 529 and return to the menu at step 530. If a new breakpoint was not set, however, control will transfer back to step 515. Step 525 will remain in an idle state until an event occurs that transfers control to step 527.

Figure 8C:
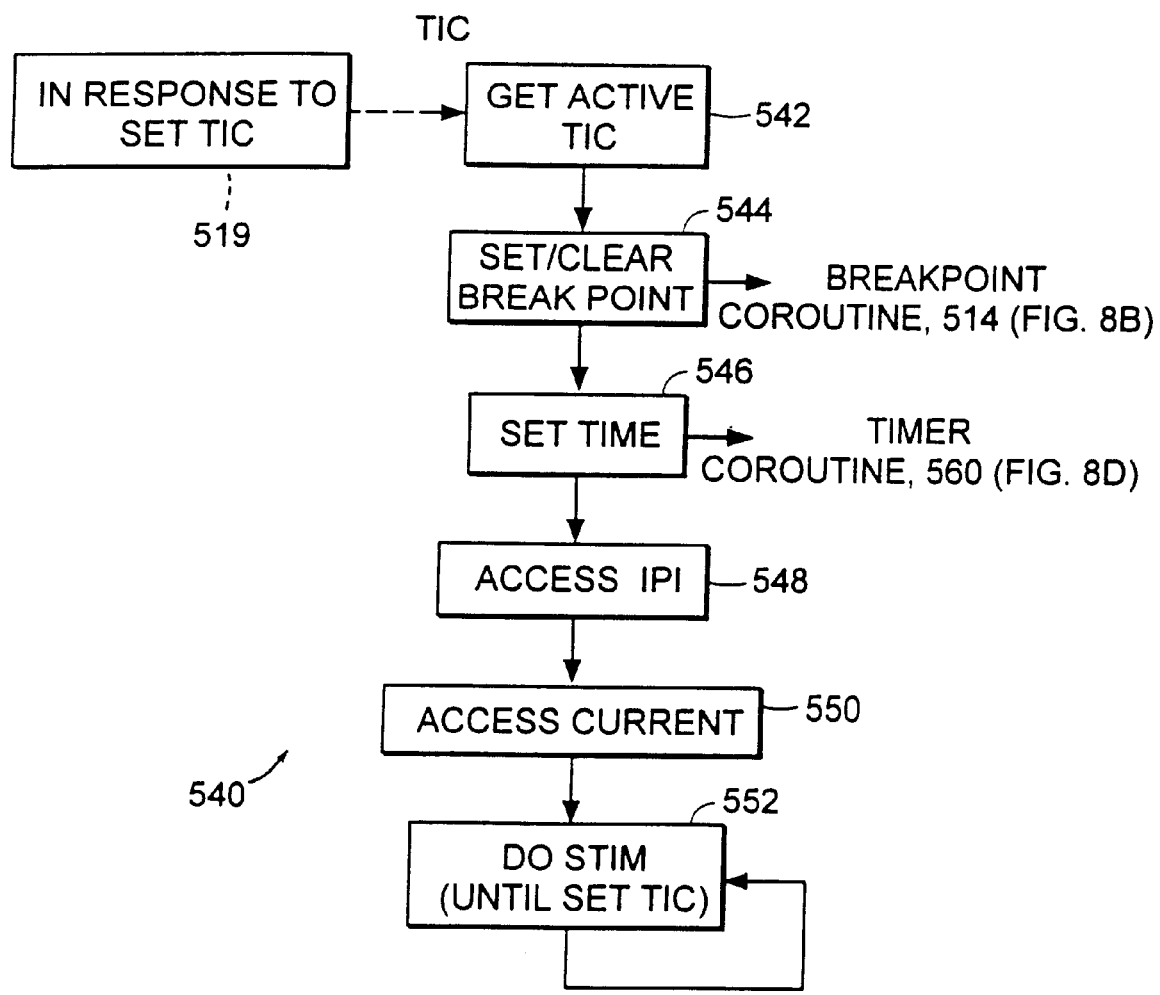
Figure 8D:
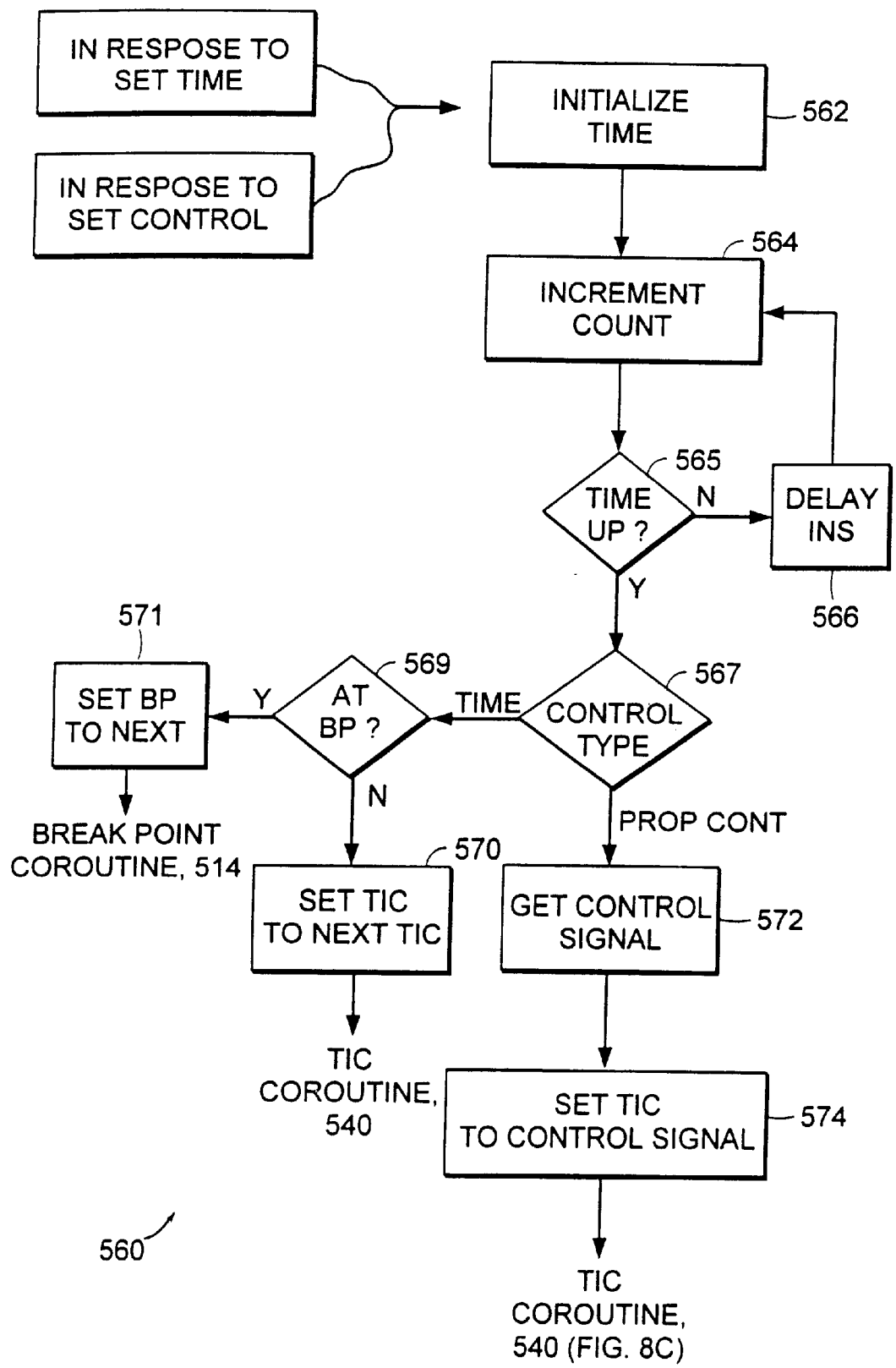

Referring now to FIG. 8C, the Tic routine is shown to include a step that fetches the active Tic routine as indicated by the Tic index at step 542. The routine checks to see if the Breakpoint is set or cleared at step 544 and will branch to the Breakpoint routine 514 if the Breakpoint is set, or if the Breakpoint is clear it will continue processing through the next step 546. At step 546, the timer routine 560 (FIG. 8D) is entered. When the timer routine returns back to the Tic routine, the Tic routine will access the IPI table at step 548 and access the current table at step 550. At step 552 it will continue to provide stimulation pulses until the Breakpoint in step 544 is set.

Referring now to FIG. 8D, the timer routine 560 is shown. Timer routine 560 is entered in response to a set time condition or a set control condition. At step 562 a time value is initialized. At step 564 a timer value is incremented by an amount determined by step 566 and at step 565 the timer value is checked to see whether a preset time value has been reached. If a time value has not been reached, the time value is incremented at step 564 by the value supplied at step 566. If the time value has been reached at step 567, the control type from the control field in the breakpoint table 308 (FIG. 6B) is checked to determine whether it is a time control or a proportional control. If it is time control, processing continues at step 569 in which the breakpoint is checked. If the breakpoint has been set at step 571, the breakpoint is set to the next breakpoint and processing continues in the breakpoint routine. If the breakpoint is not set, then processing continues at 570 to set the Tic to the next Tic and continue processing in the Tic routine 540.

If, however, the control type is determined at step t 67 to be proportional control, then the control signal specified for the particular operation is obtained and the Tic is set for the particular control signal at step 574. Processing then continues in the Tic routine at step 540 in accordance with the value of the control signal.

Having described preferred embodiments of the invention, it should be noted that other embodiments incorporating its concept may be used. It is felt, therefore, that this invention should not be limited to the disclosed embodiments, but rather should be limited only by the spirit and scope of the appended claims.

What is claimed is:

1. A method of generating stimulation patterns for execution by a functionalelectrical stimulator system comprises:
   accessing a particular stimulation pattern in a pattern table, with pattern table indexed by a pattern index; and
   accessing a Breakpoint table by the index provided from the pattern table.

2. The method of claim 1 wherein accessing a Breakpoint table further comprises:
   using information in the Breakpoint table to set a breakpoint, and to set a Tic index to index into a Tic table using a Tic routine.

3. The method of claim 1 wherein the pattern table includes a listing of a plurality of stimulation patterns, including a field identifying the pattern and a field containing a BreakPoint index to the accessed BreakPoint table.

4. The method of claim 1 wherein the BreakPoint table further includes an event field storing an index to an event routine and a control field storing a value that determines whether control is time based or proportional based.

5. The method of claim 1 wherein the table stores control and pattern information.

6. The method of claim 5 wherein the table storing the control and pattern information further comprises a menu table storing information to enable a patient to access stimulation patterns.

7. A functional electrical stimulator, comprises:
   a processor executing a program which provides from a stimulation pattern file a digital signal:
      a memory storing said stimulation pattern file, said stimulation pattern file comprising:
      a table storing control and pattern generation information and separately storing electrode characterization data for each electrode used by the portable stimulator,
   a signal processing circuit responsive to the digital signal for generating electrical stimulation pulses and coupling said pulses to electrodes used by the portable stimulator; wherein the stimulator unit operates in stand-alone mode that is permits a subject patient to select patterns via user interfaces to enable movement of muscles in the subject patient.

8. The functional electrical stimulator of claim 7 further comprises:
   a simulation parameter table that contains information to execute a stimulation pattern, the stimulation pattern table being downloaded to a device in the stimulation unit.

9. The functional electrical stimulator of claim 7 further comprises:
   a simulation parameter table that contains information that includes information for several patterns for functional stimulation exercise.

10. The functional electrical stimulator of claim 7 wherein the program resident in the stimulator executes a stimulation pattern retrieved from the stimulation parameter table in accordance with thumbswitches or the Hall effect sensors coupled to the stimulator.

11. The functional electrical stimulator of claim 10 wherein the program in the stimulator schedules and executes stimulation pulses for channels, samples and processes control signal data and performs user notification via an LED.

* * * * *